United States Patent [19]

Shapiro et al.

[11] Patent Number: 5,117,816
[45] Date of Patent: Jun. 2, 1992

[54] ANTI-SNORE DEVICE

[76] Inventors: Norman A. Shapiro, 6319 DeSoto Ave. #401; Scott E. Feldman, 6325 Topanga Canyon Blvd., Suite 424, both of, Woodland Hills, Calif. 91367

[21] Appl. No.: 637,127

[22] Filed: Jan. 3, 1991

[51] Int. Cl.⁵ .............................................. A61F 5/56
[52] U.S. Cl. .................. 128/200.24; 128/848; 128/207.14; 128/861
[58] Field of Search ...................... 128/200.24, 207.14, 128/848, 861, 862, 777

[56] References Cited

U.S. PATENT DOCUMENTS 2,669,988  2/1954  Carpenter ........................ 128/861
4,862,903  9/1989  Campbell ......................... 128/861

FOREIGN PATENT DOCUMENTS 312368  4/1989  European Pat. Off. ............ 128/848

Primary Examiner—Edgar S. Burr
Assistant Examiner—E. P. Raciti
Attorney, Agent, or Firm—Bacon & Thomas

[57] ABSTRACT

An anti-snore device as disclosed which is intended to alleviate benign loud snoring and to minimize mild to moderate sleep apnea disorders. The anti-snore device comprises a mouthpiece formed from a moldable thermal-plastic material having an upper surface portion which substantially covers the entire maxillary (upper) dentition and a lower surface portion which contacts substantially the entire mandible (lower) dentition of a user's mouth. In addition, the lower surface portion includes a downwardly extending flange intended to extend into the lingual (tongue side of the teeth) vestibule of a user in order to maintain a forward posture of the lower jaw. An airway passage is centrally located to permit adequate breathing through the mouthpiece if nasal blockage is present. An interior portion of the mouthpiece, surrounding the airway passage, is concave in shape to enable proper positioning of a user's tongue. The invention further includes a handle, preferably made from acrylic, used to aid in protecting the user during the initial fitting process. To assure the integrity of the airway slot during this fitting process, the handle includes a specifically shaped extension portion which may be fictionally secured in the airway passage while the entire mouthpiece may be maneuvered by a remote upper portion of the handle.

14 Claims, 1 Drawing Sheet

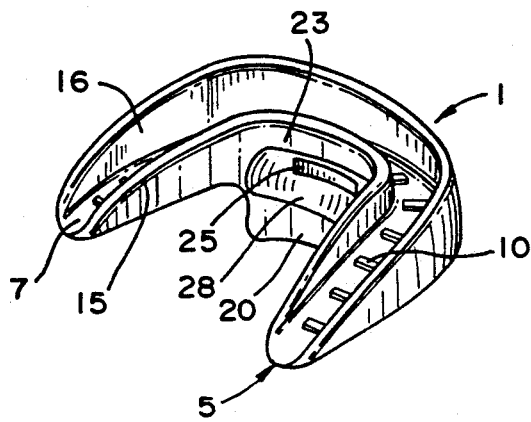
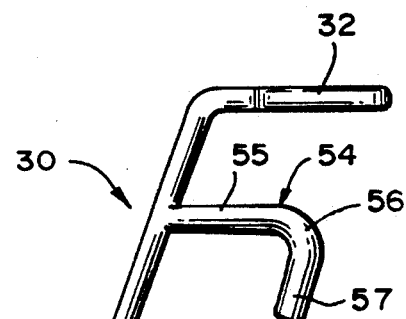
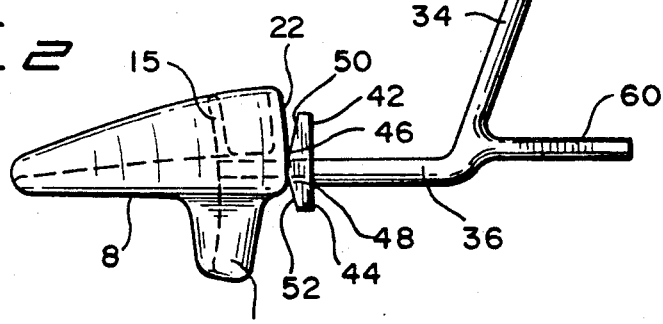
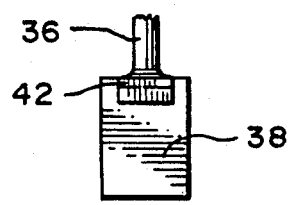
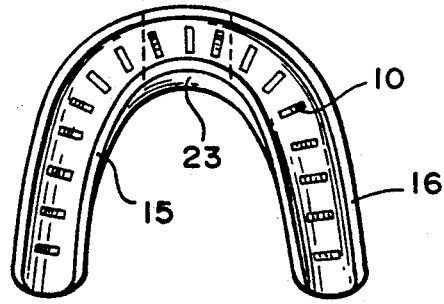
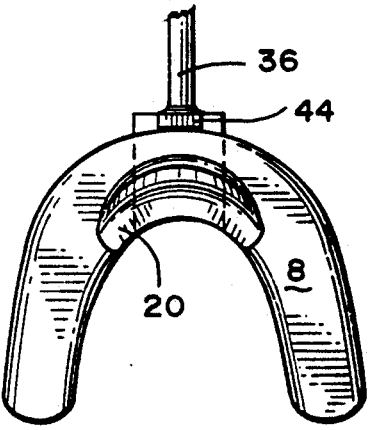

ANTI-SNORE DEVICE

BACKGROUND OF THE INVENTION

1. Field of the Invention

This invention pertains to the art of anti-snore devices and, more specifically, to a mouthpiece intended to alleviate benign loud snoring and to minimize mild to moderate sleep apnea disorders.

2. Description of the Prior Art

Various snore reducing mouthpieces are known in the prior art as represented by U.S. Pat. Nos. 746,869, 774,446, 2,424,533, 3,132,647, 3,434,470, 4,304,227, 4,669,459, 4,676,240, 4,715,368 and 4,901,737. Each of these known prior art arrangements are directed to preventing snoring and/or sleep apnea by concentrating on one aspect of the problem. For instance, of the above-cited patents, U.S. Pat. Nos. 746,869, 774,446, 2,424,533 and 3,434,470 are generally directed to mouthpiece devices which regulate the amount of air which can be inhaled and exhaled through the mouth of the user. The quantity of air is controlled so as to be insufficient to cause the necessary vibration incident to snoring and, in this manner, also regulates the flow of air through a user's nose.

U.S. Pat. Nos. 4,715,368 and 4,901,737 are generally directed to mouthpieces used in the prevention of sleep apnea disorders. Unlike the above-discussed patents which are intended to prevent snoring by reducing the intake of air through a user's mouth, these two patents disclose mouthpieces which are dentally supported and which are intended to provide for a fully opened mouth airway so that a user may unconstrictedly breath through the mouth, or through both the mouth and the nasal passages. Both of these patents are intended to space the upper and lower jaws of the user to thereby insure an air passageway into and out of the mouth. The mouthpieces disclosed in these two patents are held in a user's mouth by wiring which, not only requires professional fitting, but is uncomfortable to the user.

Another common arrangement used in the art for the prevention of snoring is represented by U.S. Pat. Nos. 3,132,647 and 4,669,459 which disclose mouthpiece arrangements intended to minimize vibrations associated with snoring. In the '647 patent, the anti-snore mouthpiece includes a downwardly extending support arm having a pad mounted on an end thereof which depresses against the user's tongue in order to maintain a space relationship between the user's palate and tongue. This arrangement, although it maintains a space relationship between the upper and lower jaws of the user and therefore permits free air passage through the user's mouth, is considerably uncomfortable to use as the tongue is depressed at a rear portion thereof.

The anti-snoring device disclosed in the '459 patent is also seen to be uncomfortable due to the fact that the mouthpiece must be clasped to upper molars on opposite sides of a user's mouth and includes a dangling button which can irritate the user as it applies pressure to the user's soft palate.

Another approach in the treatment of snoring and sleep apnea has been to provide a mouthpiece which spaces the upper and lower jaws of the user and positions the user's tongue forward of the teeth to increase the unobstructed dimension of the nasal breathing passage. Mouthpieces of this type are represented by U.S. Pat. No. 4,304,227 and 4,676,240. During use of these mouthpieces, a user's tongue is substantially maintained in this forward position which is considered awkward and uncomfortable to the user.

SUMMARY OF THE INVENTION

It is the object of the present invention to provide an improved mouthpiece device for use in the prevention of snoring and the minimization of sleep apnea which overcomes the drawbacks of the above-discussed prior art. In particular, the invention is directed to a mouthpiece which may be easily molded to conform to a user's mouth so as to be comfortable during use and which maintains the upper and lower jaws of a user in a spaced relationship.

It is another object of the invention to provide an airway passage which permits a regulated flow of air into and out of a user's mouth.

It is still another object of the invention to provide an anti-snore device which permits forward positioning of a user's tongue in order to prevent blockage of the pharyngeal airway (nasal passageway).

It is still another object of the invention to provide a means to maintain a forward posture of the lower jaw of the user.

A further object of the invention is to provide a means to handle the mouthpiece when it is being molded to conform to the specific shape of a user's mouth and which maintains the integrity of the airway passage during the molding process.

These and other objects of the invention are realized by providing a mouthpiece made from a thermoplastic material which can be heated to a softened state, inserted into a user's mouth, and thereby molded to conform to the specific jaw structure of the user. The mouthpiece is provided with inner and outer upstanding wall portions which surround the front and rear of the maxillary (upper) teeth of the user in order to provide a comfortable and non-slip fit. The airway is constituted by a slot which extends through the front and rear face of the mouthpiece to permit a regulated flow of air therethrough. A flange is provided which extends downwardly into a user's lingual vestibule so as to abut the lower teeth of a user in order to permit a forward posture of the jaw. In order to maintain the proper positioning of the user's tongue, an interior portion of the mouthpiece, surrounding the airway opening, is concave in shape. Also provided is a handle which may be utilized when heating and conforming the mouthpiece to a user's mouth. The handle includes an extension which may be inserted into the airway passage in order to maintain the integrity of the passage during the molding process.

Other objects, features and advantages of the invention shall become apparent from the following detailed description of a preferred embodiment thereof, when taken in conjunction with the drawings wherein like reference characters refer to corresponding parts in several views.

BRIEF DESCRIPTION OF THE DRAWINGS

FIG. 1 is a perspective view of an anti-snore device according to a preferred embodiment of the invention.

FIG. 2 is a side-view of the anti-snore device shown in FIG. 1 with a handle.

FIG. 3 is a top view of the anti-snore device shown in FIG. 1 with an end of the handle shown located adjacent the airway slot.

FIG. 4 is a bottom view of the anti-snore device shown in FIGS. 1 and 2 with a portion of the handle schematically represented.

DETAILED DESCRIPTION OF THE PREFERRED EMBODIMENT

The anti-snore device, according to a preferred embodiment of the invention, shall now be described with initial reference to FIGS. 1 and 2. As shown therein, the anti-snore device comprises a mouthpiece 1 including a substantially U-shaped base member 5 having an upper surface portion 7 and a lower surface portion 8. In the preferred embodiment, the entire mouthpiece is formed from a thermoplastic material such as that made by DuPont under the trademark ELVAX. As best shown in FIG. 1, the upper surface portion 7 is formed with a plurality of raised treads 10 which are spaced along its entire length. The function of these treads will be explained more fully below.

Extending upwardly from the inner and outer edges of the upper surface portion 7 are inner and outer upstanding wall portions 15 and 16 respectively. As clearly shown in FIGS. 1 and 2, inner and outer upstanding wall portions 15, 16 are tapered toward the ends of the U-shaped base member 5. Furthermore, as best shown in FIG. 3, the distance between the inner and outer upstanding wall portions 15 and 16 is less toward the user's front teeth and increases towards the ends of U-shaped base member 5 to better conform to common teeth thicknesses.

Lower surface portion 8 is formed generally flat and includes an integrally formed, downwardly extending flange 20. The flange is substantially in the shape of a flattened U as seen in FIG. 4 and is adapted to contact the rear of a user's lower front teeth in order to maintain a forward posture of the lower jaw. The flange 20 is shown to extend rearwardly only approximately one-third the length of the base member 5. Since the flange 20 is also formed from a thermoplastic material, the flange 20 must be thick enough so as to maintain the forward posture of the lower jaw, but yet must be made comfortable to the user. By extending the flange 20 rearward only approximately one-third the length of base member 5, the flange can be made of sufficient size to maintain this forward posture and, in combination with the specific shape of the flange, can be comfortable to the user. This forward posture is particularly important since when a human assumes a horizontal position, the lower jaw has a tendency to shift. This shift is associated with the vibrations which occur during snoring.

As best shown in FIGS. 1 and 2, the mouthpiece 1 includes a front face 22 and rear face 23. Extending through from front face 22 to rear face 23 is an airway passage 25. In the preferred embodiment represented, airway passage 25 generally takes the form of an elongated slot which is rectangular in cross-section. By this construction, the airway slot may be made as large as necessary to provide unrestricted air flow through the user's mouth without weakening the integrity of base 5. As also seen in FIG. 1, formed about airway passage 25 is a concavity 28. The concavity 28 is formed in rear face 23 of base member 5 and surrounds the entire periphery of airway passage 25. For the reasons which will be explained more fully below, concavity 28 permits forward positioning of a user's tongue.

As previously stated, mouthpiece 1 is formed from a thermoplastic material and can be molded to conform to the specific shape of a user's mouth. In order to carry out this function, the mouthpiece is intended to be inserted into a heated liquid such as water which will tend to soften the thermoplastic material. A user can then insert the softened mouthpiece 1 into his/her mouth and, while biting down, the mouthpiece 1 will begin to conform to the user's mouth. In practice, it has been found that after just a few repetitions of the heating and molding steps, the mouthpiece conforms adequately to a user's mouth and can then be comfortably maintained therein. For use during this heating and molding process, the invention includes a handle member 30 which, in the preferred embodiment, is injected molded from acrylic.

As shown best in FIGS. 2 and 3, handle 30 includes an upper portion 32 adapted to be held by the user during the initial fitting process of mouthpiece 1, an intermediate portion 34 and a lower portion 36. Upper portion 32 and lower portion 36 are maintained substantially parallel and spaced by intermediate portion 34 so that the risk of contact of the user's hand with the heating liquid is minimized.

Integrally formed with lower portion 36 of handle 30 is an extension 38. Extension 38 conforms in shape to the airway passage 25. In the preferred embodiment, extension 38 is flat and generally rectangular. During the initial fitting process of the mouthpiece 1 to a user's mouth, extension 38 is inserted into airway passage 25 to insure integrity of the airway during the fitting process. After the mouthpiece 1 has been fitted to a user's mouth and cooled to ambient temperature so as to no longer be soft, extension 38 can be removed from airway passage 25.

In addition, located at the junction point between lower portion 36 and extension 38 of handle 30 are a pair of tabs 42, 44. As shown in FIG. 2, tab 42 extends upwardly and tab 44 extends downwardly. Each tab 42, 44 can perform a dual function, the first of which is as a stop to prevent overinsertion of extension 38 into airway passage 25. For this purpose, each tab 42, 44 has an associated vertical section 46, 48 respectively. Although both upper and lower tabs are present in the preferred embodiment, it is possible to utilize only a single stop member to perform this function. Each tab 42, 44 also includes a sloped portion 50, 52 which aids in the proper positioning of the mouthpiece during the fitting process as will be described more fully below.

Since extension 38 is generally symmetrical, handle 30 may be utilized with mouthpiece 1 during the initial fitting process in the upright position as shown in FIG. 2 or inverted while still performing the function of maintaining the integrity of the airway passage and protecting the user So long as two tabs 42, 44 are utilized, one of the tabs 42, 44 will extend downwardly in front of flange 20 as shown in FIG. 2. When fitting the mouthpiece, the front teeth of the user may ride up slope portion 52 to assure proper jaw positioning.

Also in the preferred embodiment as represented in FIG. 2, an elbow member 54 is integrally formed with an upper section of intermediate portion 34. Elbow member 54 includes a horizontal section 55 which extends generally parallel to upper portion 32, a curved section 56 and a downwardly extending section 57. In addition, a lower section of intermediate portion 34 includes an integrally formed, rewardly extending stabilizing member 60. Elbow member 54 is intended to support the handle 30 and mouthpiece 1 on a convention pot (not shown) during the heating process by being placed about the pot's rim. Stabilizing member 60 is adapted to abut an interior side of the pot (not shown) in order to prevent shifting of the handle 30 and mouthpiece 1.

During the heating and molding process, the raised treads 10 on upper surface portion 7 of base 5 provide an enlarged heating surface area and are quickly softened to provide additional material which can be used to conform the upper surface portion 7 with the upper dentition of the user. Therefore, treads 10 provide more material which will provide for a better fit so that the mouthpiece 1 will not be inclined to shift during use. In addition, base 5 is intended to extend rearward substantially the entire dentition length of the user's mouth to also provide for a more secure fit. These features are emphasized since small mouthpiece arrangements run the risk of being jarred loose during use and may even cause clogging of the airway passage.

Based on the above description, it can be readily seen that the present anti-snore device constitutes a mouthpiece which can be easily made to comfortably conform to a user's mouth, held against unwanted movement during use since the base 5 covers substantially the entire maxillary (upper) dentition and the entire mandibular (lower) dentition and treads 10 provide additional surface material so that the mouthpiece actually becomes indigited with the user's entire maxillary dentition. In addition, since flange 20 is arranged to extend into the arranged lingual (tongue side of the teeth) vestibule, the user's lower jaw is maintained in a forward posture. The airway passage 25 is essentially positioned to optimize airflow even if nasal blockage is present. Furthermore, with the inclusion of concavity 28 about airway passage 25 on the rear face 23 of base 5 mouthpiece 1 permits positioning of the tip of the user's tongue in a more forward posture. Finally, handle 30 includes means (extension 38) to assure integrity of the airway passage 25 as well as means (tabs 42, 44) to aid in the proper positioning of the user's jaw during the fitting process.

It is to be understood that the form of the invention shown and described are to be taken as a preferred embodiment thereof and various changes in shape, material and size may be resorted to without departing from the spirit of the invention or scope as defined in the following claims.

We claim:

1. A device which may be molded to fit a particular user for the prevention of benign loud snoring and the minimization of apnea disorders comprising:
   a substantially U-shaped base member having a front face, a rear face, and upper and lower surface portions adapted to be engaged with the upper and lower dentitions of a user;
   inner and outer upstanding wall portions extending upwardly from inner and outer edges of said upper surface portion;
   a flange extending downwardly from the lower surface portion of said base member and adapted to maintain forward posture of a user's lower jaw;
   an airway passage extending through a central portion of the face of said base member; and
   airway passage integrity means removably located in said airway passage to assure non-deformation of said airway passage when said device is molded to fit a particular user.

2. A device as recited in claim 1 wherein said airway passage integrity means constitutes an extension of a handle used when said device is molded to fit the particular user.

3. A device as recited in claim 2 wherein said handle includes an upper gripping portion, an intermediate portion and a lower portion, said extension being integrally formed with said lower portion.

4. A device as recited in claim 3 further including a concavity formed in the rear face of said base member, said concavity surrounding the entire periphery of said airway passage in order to permit forward positioning of a user's tongue.

5. A device as recited in claim 4 wherein said base member extends over substantially the entire dentition of the user and said upstanding wall portions taper off towards the ends of said U-shaped base member.

6. A device as recited in claim 5 wherein said upper surface portion includes a plurality of spaced, upwardly projecting tread members.

7. A device as recited in claim 6 wherein said airway passage constitutes a slot which is substantially rectangular in cross-section.

8. A device as recited in claim 4 wherein said handle includes at least one tab extending substantially perpendicular to said extension.

9. A device as recited in claim 8 wherein said at least one tab includes a substantially vertical section and a sloped section and wherein said sloped section is intended to guide the user's front teeth to a desired position during the fitting process.

10. A device as recited in claim 9 wherein said upper surface portion includes a plurality of spaced, upwardly projecting tread members.

11. A device as recited in claim 3 wherein said handle includes at least one tab extending substantially perpendicular to said extension.

12. A device as recited in claim 11 wherein said at least one tab includes a substantially vertical section and a sloped section and wherein said sloped section is intended to guide the user's front teeth to a desired position during the fitting process.

13. A device as recited in claim 12 wherein said handle further includes support means adapted to engage an external object in order to support said device.

14. A device as recited in claim 13 wherein said support means comprises an elbow member and a stabilizing member both located along said intermediate portion in a spaced relationship.

* * * * *